US009566435B2

(12) United States Patent
Polak (10) Patent No.: US 9,566,435 B2
(45) Date of Patent: Feb. 14, 2017

(54) TINNITUS FITTING METHOD IN CI AND ABI PATIENTS

(71) Applicant: MED-EL Elektromedizinische Geraete GmbH, Innsbruck (AT)

(72) Inventor: Marek Polak, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 0 days.

(21) Appl. No.: 14/927,524

(22) Filed: Oct. 30, 2015

(65) Prior Publication Data

US 2016/0121117 A1    May 5, 2016

Related U.S. Application Data

(60) Provisional application No. 62/073,147, filed on Oct. 31, 2014.

(51) Int. Cl.
*A61N 1/36* (2006.01)
*A61N 1/05* (2006.01)

(52) U.S. Cl.
CPC ......... *A61N 1/36032* (2013.01); *A61N 1/0541* (2013.01)

(58) Field of Classification Search
None
See application file for complete search history.

(56) References Cited

U.S. PATENT DOCUMENTS

| 2006/0036297 | A1 | 2/2006 | Seidman |
| 2011/0077712 | A1 | 3/2011 | Killian |
| 2011/0105967 | A1 | 5/2011 | Zeng et al. |
| 2011/0295166 | A1 | 12/2011 | Dalton |

OTHER PUBLICATIONS

International Searching Authority, Authorized Officer Shane Thomas, International Search Report and Written Opinion, PCT/US15/58180, date of mailing Jan. 21, 2016, 12 pages.

*Primary Examiner* — Brian T Gedeon
*Assistant Examiner* — Ankit D Tejani
(74) *Attorney, Agent, or Firm* — Sunstein Kann Murphy & Timbers LLP (57) ABSTRACT

A method is described for adjusting hearing implant operating parameters for electrode contacts in an implantable electrode array to minimize tinnitus in an implanted patient. A channel tinnitus masking stimulation level is measured for each electrode contact at which maximum tinnitus masking occurs, $Y_{tin,n}$. A channel threshold stimulation level also is measured for each electrode contact that represents a lowest detectable stimulation level, $T_{meas,n}$. And a channel maximum stimulation level is measured for each electrode contact that represents a maximum comfortable stimulation level, $MCL_{meas,n}$. Channel threshold stimulation level $T_n$ and channel maximum stimulation level $MCL_n$ are then adjusted for each electrode contact as a function of the channel tinnitus masking stimulation level $Y_{tin,n}$ and tinnitus masking stimulation levels for adjacent electrode contacts, $Y_{tin,adj}$.

11 Claims, 8 Drawing Sheets

TINNITUS FITTING METHOD IN CI AND ABI PATIENTS

This application claims priority from U.S. Provisional Patent Application 62/073,147, filed Oct. 31, 2014, which is incorporated herein by reference in its entirety.

TECHNICAL FIELD

The present invention relates to medical implants, and more specifically to fit customization in audio prosthesis systems such as cochlear implant systems.

BACKGROUND ART

Figure 1:
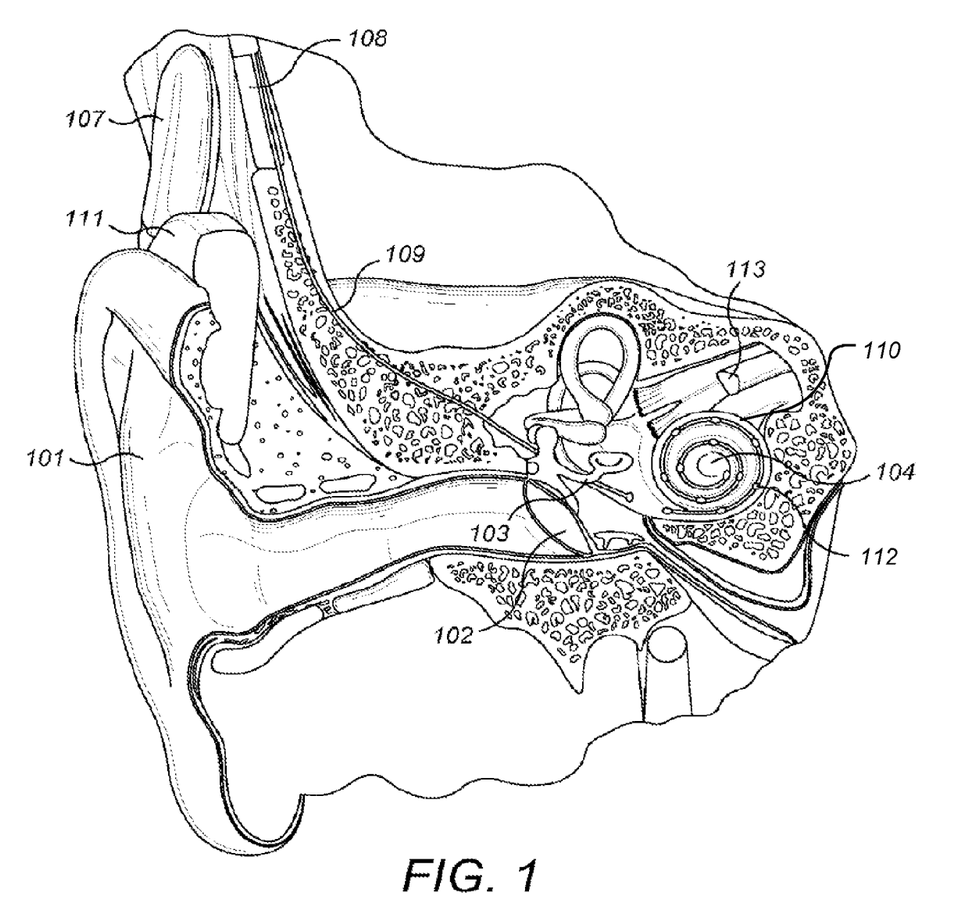
FIG. 1 shows anatomical structures in a human ear having a cochlear implant system.

A normal ear transmits sounds as shown in FIG. 1 through the outer ear 101 to the tympanic membrane (eardrum) 102, which moves the bones of the middle ear 103 (malleus, incus, and stapes) that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, auditory prostheses have been developed. For example, when the impairment is related to operation of the middle ear 103, a conventional hearing aid may be used to provide acoustic-mechanical stimulation to the auditory system in the form of amplified sound. Or when the impairment is associated with the cochlea 104, a cochlear implant with an implanted electrode contact can electrically stimulate auditory nerve tissue with small currents delivered by multiple electrode contacts distributed along the electrode.

FIG. 1 also shows some components of a typical cochlear implant system which includes an external microphone that provides an audio signal input to an external signal processor 111 where various signal processing schemes can be implemented. The processed signal is then converted into a digital data format, such as a sequence of data frames, for transmission into the implant 108. Besides receiving the processed audio information, the implant 108 also performs additional signal processing such as error correction, pulse formation, etc., and produces a stimulation pattern (based on the extracted audio information) that is sent through an electrode lead 109 to an implanted electrode array 110. Typically, this electrode array 110 includes multiple electrodes on its surface that provide selective stimulation of the cochlea 104.

For an audio prosthesis such as a cochlear implant to work correctly, some patient-specific operating parameters need to be determined in a fit adjustment procedure where the type and number of operating parameters are device dependent and stimulation strategy dependent. Possible patient-specific operating parameters for a cochlear implant include:

$THR_1$ (lower detection threshold of stimulation amplitude) for Electrode 1
$MCL_1$ (most comfortable loudness) for Electrode 1
Phase Duration for Electrode 1
$THR_2$ for Electrode 2
$MCL_2$ for Electrode 2
Phase Duration for Electrode 2
. . .
Pulse Rate
Number of fine structure channels
Compression
Parameters of frequency—>electrode mapping
Parameters describing the electrical field distribution One common method for fit adjustment is to behaviorally find the threshold (THR) and most comfortable loudness (MCL) value for each separate electrode contact. See for example, Rätz, *Fitting Guide for First Fitting with MAE-STRO* 2.0, MED-EL, Fürstenweg 77a, 6020 Innsbruck, 1.0 Edition, 2007. AW 5420 Rev. 1.0 (English_EU); incorporated herein by reference. Other alternatives/extensions are sometimes used with a reduced set of operating parameters; e.g. as suggested by Smoorenburg, *Cochlear Implant Ear Marks*, University Medical Centre Utrecht, 2006; and U.S. Patent Application 20060235332; which are incorporated herein by reference. Typically each stimulation channel is fitted separately without using the information from already fitted channels. The stimulation current on a given electrode typically is increased in steps from zero until the MCL or THR is reached.

One approach for an objective measurement of MCLs and THLs is based on the measurement of the ECAPs (Electrically Evoked Compound Action Potentials), as described by Gantz et al., *Intraoperative Measures of Electrically Evoked Auditory Nerve Compound Action Potentials*, American Journal of Otology 15 (2):137-144 (1994), which is incorporated herein by reference. In this approach, a recording electrode in the scala tympani of the inner ear is used. The overall response of the auditory nerve to an electrical stimulus is measured very close to the position of the nerve excitation. This neural response is caused by the superposition of single neural responses at the outside of the axon membranes. The amplitude of the ECAP at the measurement position is typically in the ranges of µV. When performing objective measurements such as ECAP measurements in existing cochlear implant systems, usually each electrode contact of the implantable electrode array is scanned separately, increasing the stimulation signal current on an electrode contact in steps from zero or a very low level until an ECAP response is detected.

Besides hearing loss, another related hearing-related affliction is tinnitus, which is the perception of sound ("ringing of the ears") when no external sound is present. While often referred to as "ringing," but it take many forms such as high-pitched whining sound, electric buzzing, hissing, humming, tinging or whistling sound, or as ticking, clicking, roaring, etc. The perception of tinnitus sounds may range from a quiet background noise to one that can be heard even over loud external sounds. Tinnitus is often a subjective phenomenon. Tinnitus can be perceived in one or both ears or in the head.

There are various existing methods and systems for treatment of tinnitus, including use of therapeutic drugs, masking by acoustical stimulation, mechanical stimulation or by a special implant with direct electrical stimulation of the cochlea.

SUMMARY

Embodiments of the present invention are directed to adjusting hearing implant operating parameters for electrode contacts in an implantable electrode array to minimize tinnitus in an implanted patient. A channel tinnitus masking stimulation level is measured for each electrode contact at which maximum tinnitus masking occurs, $Y_{tin,n}$. A channel threshold stimulation level also is measured for each electrode contact that represents a lowest detectable stimulation level, $T_{meas,n}$. And a channel maximum stimulation level is measured for each electrode contact that represents a maximum comfortable stimulation level, $MCL_{meas,n}$. Channel threshold stimulation level $T_n$ and channel maximum stimulation level $MCL_n$ are then adjusted for each electrode contact as a function of the channel tinnitus masking stimulation level $Y_{tin,n}$ and tinnitus masking stimulation levels for adjacent electrode contacts, $Y_{tin,adj}$. Channel threshold stimulation level $T_n$ and channel maximum stimulation level $MCL_n$ may be derived from subjective and/or objective measurement methods.

In specific embodiments, the adjusting function may adjust the stimulation levels for a given electrode contact based on a channel mean stimulation level $Z_n$, which is defined as a sum of the measured channel threshold stimulation level $T_{meas,n}$ and half the difference between the measured maximum stimulation level, $MCL_{meas,n}$ and the measured channel threshold stimulation level $T_{meas,n}$: $Z_n = T_{meas,n} + (MCL_{meas,n} - T_{meas,n})/2$. Channel tinnitus then is defined as low when the channel tinnitus masking stimulation level $Y_{tin,n}$ is less than channel mean stimulation level $Z_n$, and high when the channel tinnitus masking stimulation level $Y_{tin,n}$ is greater than channel mean stimulation level $Z_n$. This definition of $Z_n$ shall be regarded as an example. For various reasons $Z_n$ may assume values which are within ±20% of the value calculated according to the formula above. However, $Z_n$ can always be regarded as a measure of a midline value between $MCL_{meas,n}$ and $T_{meas,n}$.

The adjustment function may adjust the channel threshold stimulation level $T_n$ and channel maximum stimulation level $MCL_n$ to be equal to the measured channel threshold stimulation level $T_{meas,n}$ and channel maximum stimulation level $MCL_{meas,n}$ for an electrode contact when channel tinnitus for the electrode contact and the adjacent electrode contacts is low. On the other hand, when channel tinnitus for the electrode contact is low, and channel tinnitus for at least one of the adjacent electrode contacts is high, the adjustment function may adjust the channel threshold stimulation level $T_n$ to be greater than the measured channel threshold stimulation level $T_{meas,n}$ for the electrode contact. When channel tinnitus for the electrode contact is high, the adjustment function may adjust the channel threshold stimulation level $T_n$ to be less than the measured channel threshold stimulation level $T_{meas,n}$. And the adjustment function may adjust the channel maximum stimulation level $MCL_n$ to be greater than the measured channel maximum stimulation level $MCL_{meas,n}$ for an electrode contact when the channel tinnitus masking stimulation level $Y_{tin,n}$ equals or exceeds the measured channel maximum stimulation level $MCL_{meas,n}$. Typically, there may be a dynamic range of at least 1 dB between the adjusted channel threshold stimulation level $T_n$ and the channel maximum stimulation level $MCL_n$.

In specific embodiments, the electrode array may be a cochlear implant electrode array or an auditory brainstem implant (ABI) electrode array. The electrode contacts may be arranged on the electrode array in a one-dimensional array (e.g., as in a cochlear implant), in a two-dimensional array (e.g., as in an ABI implant).

Embodiments also include a hearing implant fitting system using a method according to any of the above, and a computer program product implemented in a computer readable storage medium for fitting an implanted electrode of a hearing implant to an implanted patient and including program code for performing a method according to any of the above.

DETAILED DESCRIPTION

Embodiments of the present invention are directed to a method and a corresponding system for determining patient specific operating parameters for electrode contacts in a hearing implant electrode array that minimizes tinnitus. Direct electrical stimulation of the auditory pathway neurons immediately adjacent to the damaged area is used to minimize the projections of the tinnitus and to allow for maximum reorganization of the brainstem and auditory pathway to the stage prior to the occurrence of the tinnitus. In specific embodiments, the hearing implant may be a cochlear implant (CI) or an auditory brainstem implant (ABI). In such cases, the electrode contacts would be arranged on the electrode array in a one-dimensional or a two-dimensional array respectively.

Figure 2:
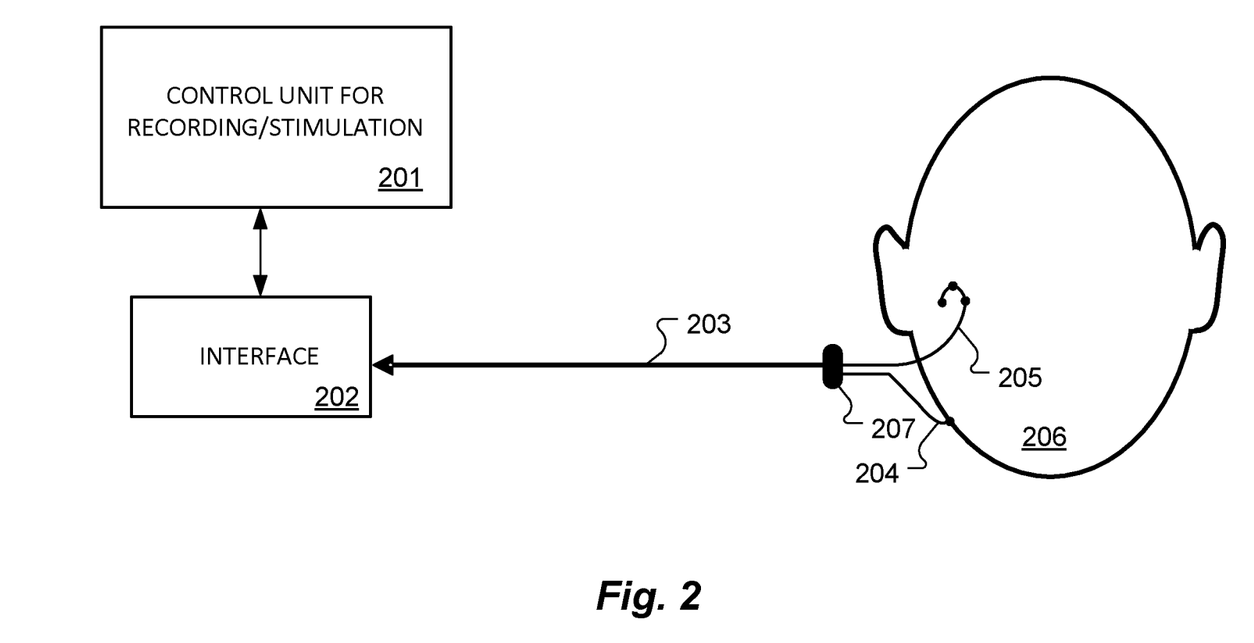
FIG. 2 shows a block diagram of a cochlear implant fitting system according to one specific embodiment of the present invention.

FIG. 2 shows a block diagram of a cochlear implant fitting system configured to perform such tinnitus minimizing. Control Unit 201 for Recording and Stimulation, for example, a Med-El Maestro Cochlear Implant (CI) system, generates stimulation signals and analyzes response measurements. Connected to the Control Unit 201 is an Interface Box 202, for example, a Diagnostic Interface System such as the DIB II conventionally used with the Maestro CI system that formats and distributes the input and output signals between the Control Unit 201 and the system components implanted in the Patient 206. For example, as shown in FIG. 2, there may be an Interface Lead 203 connected at one end to the Interface Box 202 and at the other end having Electrode Plug 207 that then divides into a Cochlear Implant Electrode 204 and an Extra-Cochlear Ground Electrode 205. After delivering a stimulation pulse, a Cochlear Implant Electrode 204 may be used as a sensing element to determine current and voltage characteristics of the adjacent tissue.

Figure 3:
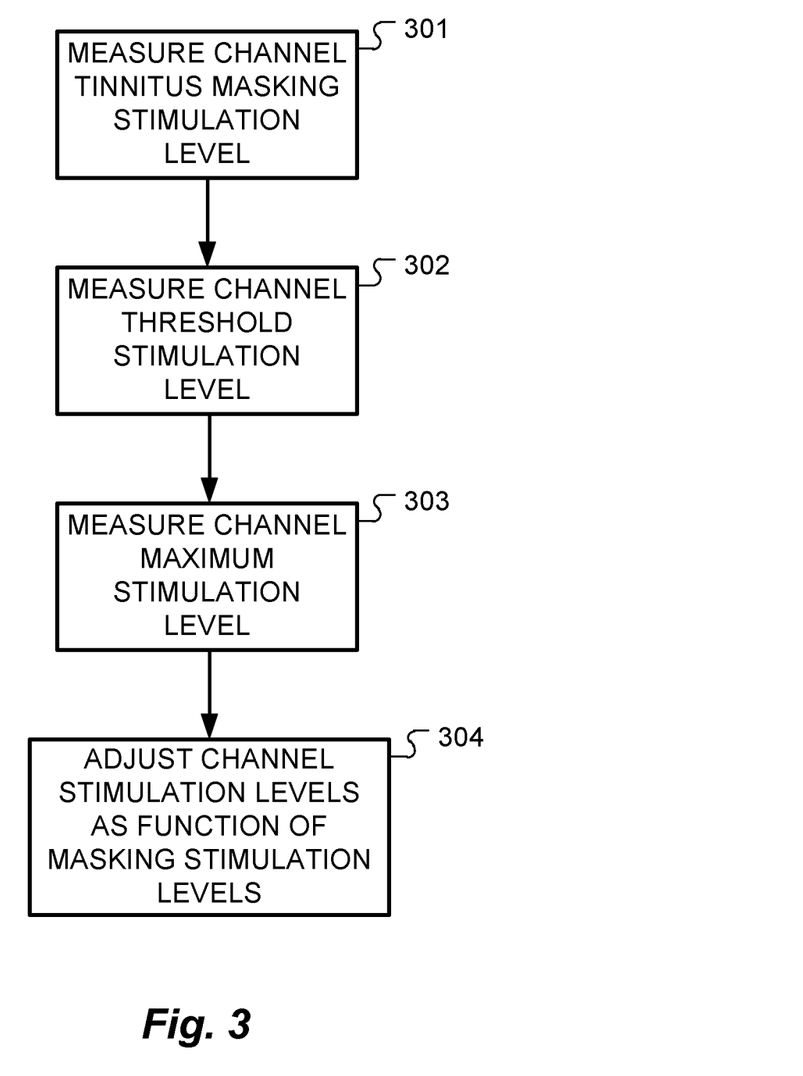
FIG. 3 shows various steps in a process for adjusting hearing implant operating parameters according to an embodiment of the present invention.

FIG. 3 shows various logical steps in an algorithm for determining cochlear implant operating parameters for each electrode contact so as to minimize tinnitus. First, step 301, for each electrode contact, a channel tinnitus masking stimulation level is measured at which maximum tinnitus masking occurs, $Y_{tin,n}$ on that electrode contact. That is, after surgical insertion of the electrode array into the target neural tissue, for each identified electrode contact location/frequency it is recorded when the tinnitus is entirely or maximally masked. The level of the respective presented probe stimulus is assigned to $Y_{tin,n}$, wherein n denotes the number of the respective electrode contact channel.

A channel threshold stimulation level also is measured for each electrode contact, step 302, that represents a lowest detectable stimulation level, $T_{meas,n}$ on that electrode contact. And a channel maximum stimulation level is measured, step 303, for each electrode contact that represents a maximum comfortable stimulation level, $MCL_{meas,n}$ n on that electrode contact. These measurements may be taken by either by appropriate subjective (psychophysical) and/or objective (e.g., ECAP) fitting methods. The inventors' experience shows that the maximum tinnitus level is always at or below the MCL. Thus, if the entire audible frequency range is stimulated, the stimulation level at which the tinnitus is masked completely or maximally can be obtained.

Then step 304 adjusts the channel threshold stimulation level $T_n$ and channel maximum stimulation level $MCL_n$ for each electrode contact as a function of the channel tinnitus masking stimulation level $Y_{tin,n}$ and tinnitus masking stimulation levels for adjacent electrode contacts, $Y_{tin,adj}$. For example, the adjusting function in step 304 may adjust the stimulation levels for a given electrode contact based on a channel mean stimulation level $Z_n$, which is defined as a sum of the measured channel threshold stimulation level $T_{meas,n}$ and half the difference between the measured maximum stimulation level, $MCL_{meas,n}$ and the measured channel threshold stimulation level $T_{meas,n}$: $Z_n = T_{meas,n} + (MCL_{meas,n} - T_{meas,n})/2$. Channel tinnitus then is defined as "low" when the channel tinnitus masking stimulation level $Y_{tin,n}$ is less than channel mean stimulation level $Z_n$, and "high" when the channel tinnitus masking stimulation level $Y_{tin,n}$ is greater than channel mean stimulation level $Z_n$. In addition, for CI electrodes, the meaning of "adjacent" electrode contacts for a given electrode contact n is n+1 or n−1 of the 1-dimensional cochlear implant electrode array (even in cases of unequal spacing). For ABI electrodes, "adjacent" electrode contacts for a given electrode contact n refers to electrode contacts having the smallest geographical distance to that electrode contact n within a predefined interval. Since an ABI electrode array is an electrode paddle with a 2 dimensional electrode array, this means that there may be more than two adjacent electrode contacts.

In such an arrangement, when channel tinnitus for an electrode contact and the adjacent electrode contacts both are low, the adjustment function then may adjust the channel threshold stimulation level $T_n$ and channel maximum stimulation level $MCL_n$ to be equal to the measured channel threshold stimulation level $T_{meas,n}$ and channel maximum stimulation level $MCL_{meas,n}$ for that electrode contact. On the other hand, when channel tinnitus for a given electrode contact is low, but the channel tinnitus for at least one of the adjacent electrode contacts is high, the adjustment function then may adjust the channel threshold stimulation level $T_n$ to be greater than the measured channel threshold stimulation level $T_{meas,n}$ for that electrode contact. When channel tinnitus for a given electrode contact is high, the adjustment function then may adjust the channel threshold stimulation level $T_n$ to be less than the measured channel threshold stimulation level $T_{meas,n}$. And the adjustment function may adjust the channel maximum stimulation level $MCL_n$ to be greater than the measured channel maximum stimulation level $MCL_{meas,n}$ for an electrode contact when the channel tinnitus masking stimulation level $Y_{tin,n}$ equals or exceeds the measured channel maximum stimulation level $MCL_{meas,n}$. Typically, there may be a dynamic range of at least 1 dB between the adjusted channel threshold stimulation level $T_n$ and the channel maximum stimulation level $MCL_n$.

For example, for electrode contact channels with no tinnitus: $T_n = w_n \times T_{n,meas}$, where $w_n$ may vary from 1 to $Z_n/T_{n,meas}$ and $w_n$ may assume any value within the range. For electrode contact channels with tinnitus, $T_n^* = w_n^* \times Y_{n,tin}$, where $w_n^*$ may vary from 1 to $T_{n,meas}/Y_{n,tin}$ and $w_n^*$ may assume any value within the range, and $MCL_n = v_n \times MCL_{n,meas}$, where $v_n$ may vary from 1 to 1.3, preferably from 1 to 1.15. In some embodiments, there may be a given electrode contact channel k located between another electrode contact channel i with very high (very loud) tinnitus and another electrode contact channel j with low or no tinnitus. In such circumstances, the $MCL_k$ value may be raised to be on a linearly fitted curve between $MCL_i$, and $MCL_j$.

Figure 4:
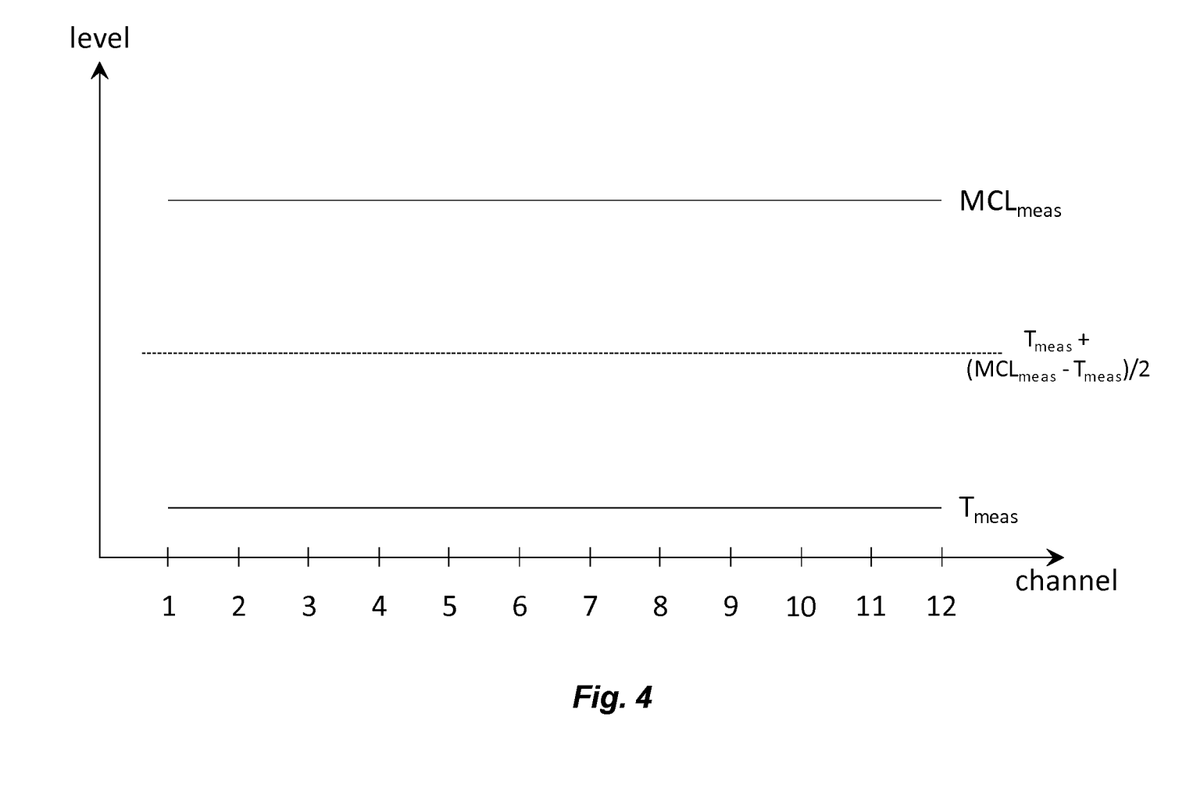
FIG. 4 shows a simplified graph of channel operating parameters for a 12 channel hearing implant electrode.

In the following examples and figures, for simplicity of the explanation $T_{n,meas}$ and $MCL_{n,meas}$ all have the same values for all electrode contact channels n, as shown in FIG. 4. It then follows that all the electrode contacts channels n also have the same mean value $Z_n = T_{meas,n} + (MCL_{meas,n} - T_{meas,n})/2$. In real life circumstances, some or all values of $T_{n,meas}$ and $MCL_{n,meas}$ may of course be different from one other. And in all the following figures, the dashed lines for $T_n$ and $MCL_n$ are just imaginary guides to the eyes.

Figure 5:
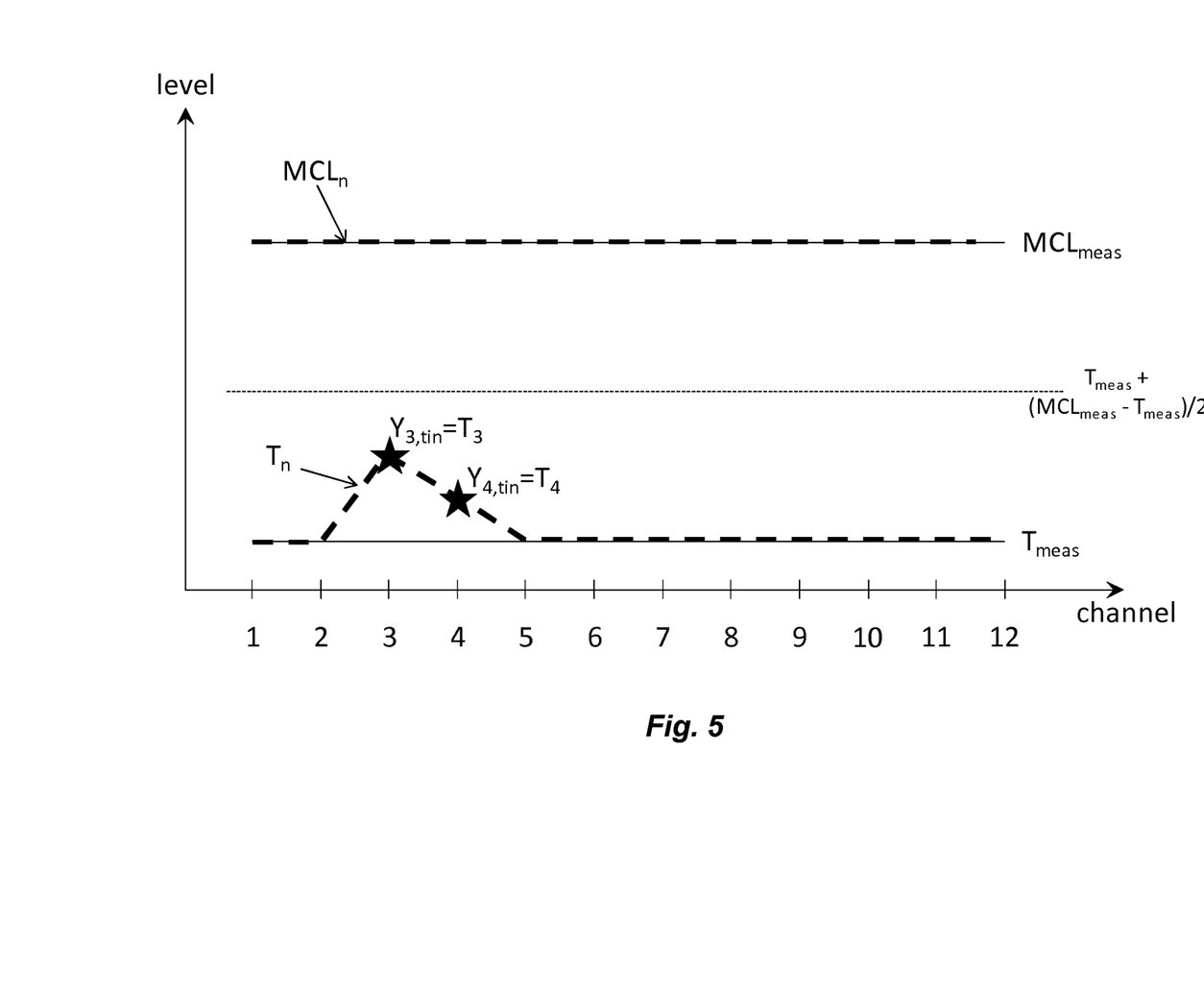
FIG. 5 shows a simplified graph of channel operating parameters with mild tinnitus measured on two electrode contact channels.

FIG. 5 shows a simplified graph of channel operating parameters with no tinnitus perceived on most of the electrode contact channels, and just mild tinnitus ($Y_{n,tin} < Z_n$) perceived on electrode contact channels 3 and 4. On all the electrode contact channels, the adjusted channel maximum stimulation level $MCL_n$ is set to $MCL_{n,meas}$ where $v_n = 1$. On the electrode contact channels with no perceived tinnitus, the adjusted channel threshold stimulation level $T_n$ is set to $T_{n,meas}$ where $w_n = 1$, while on the electrode contact channels 3 and 4 with mild perceived tinnitus, the adjusted channel threshold stimulation level $T_n$ is set to the tinnitus weighted channel threshold stimulation level $T_n^* = w_n^* Y_n$ where $w_n^* = 1$.

Figure 6:
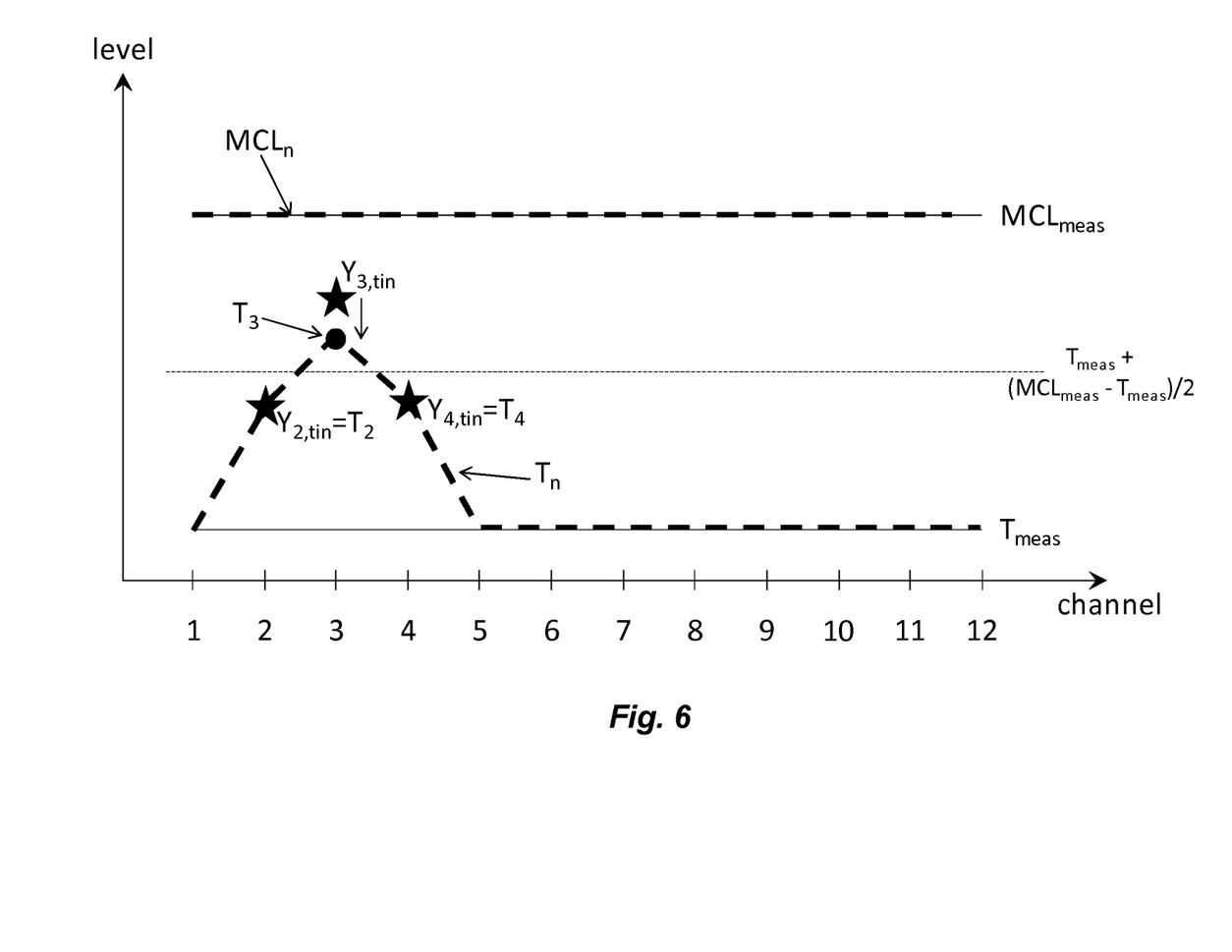
FIGS. 6 and 7 show simplified graphs of channel operating parameters with high tinnitus measured on some electrode contact channels.

FIG. 6 shows a simplified graph of channel operating parameters with high tinnitus ($Y_{n,tin} > Z_n$) perceived on electrode contact channel 3, mild tinnitus ($Y_{n,tin} < Z_n$) perceived on electrode contact channels 2 and 4, and no tinnitus perceived on the remaining electrode contact channels. Once again, on all the electrode contact channels, the adjusted channel maximum stimulation level $MCL_n$ is set to $MCL_{n,meas}$ where $v_n = 1$. On electrode contact channels 1 and 5-12, there is no perceived tinnitus and the adjacent channels n+1 and n−1 have no or low perceived tinnitus, and the adjusted channel threshold stimulation level $T_n$ is set to $T_{n,meas}$ where $w_n = 1$ just as in FIG. 5. For electrode contact channels 2 and 4, there is low tinnitus perceived and again as in FIG. 5, the adjusted channel threshold stimulation level $T_n$ is set to the tinnitus weighted channel threshold stimulation level $T_n^* = w_n^* Y_n$ where $w_n^* = 1$. For electrode contact channel 3, there is high perceived tinnitus, and the adjusted channel threshold stimulation level $T_n$ is set to the tinnitus weighted channel threshold stimulation level $T_n^* = w_n^* Y_n$ and $w_n^* < 1$.

Figure 7:
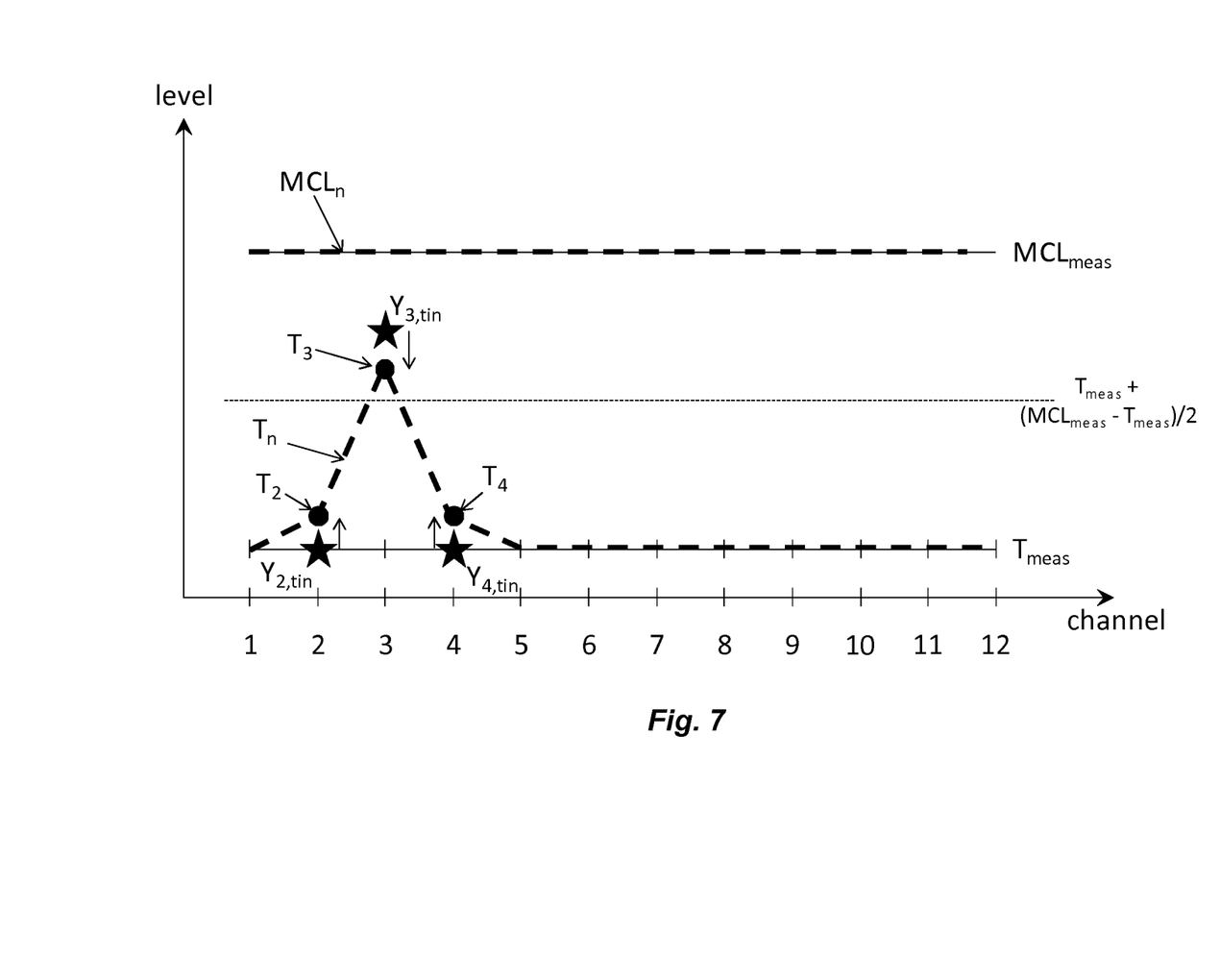

FIG. 7 shows a simplified graph of channel operating parameters with circumstances to those in FIG. 6, with high tinnitus ($Y_{n,tin} > Z_n$) perceived on electrode contact channel 3 only and no tinnitus perceived on any of the other electrode contact channels. In that case, most of the electrode contact channels will be set as in FIG. 6, but electrode contact channels 2 and 4 where there is no perceived tinnitus, but which are adjacent to electrode contact channel 3 with high perceived tinnitus will have their respective adjusted channel threshold stimulation levels $T_n$ set to $T_{n,meas}$ where $w_n>1$.

Figure 8:
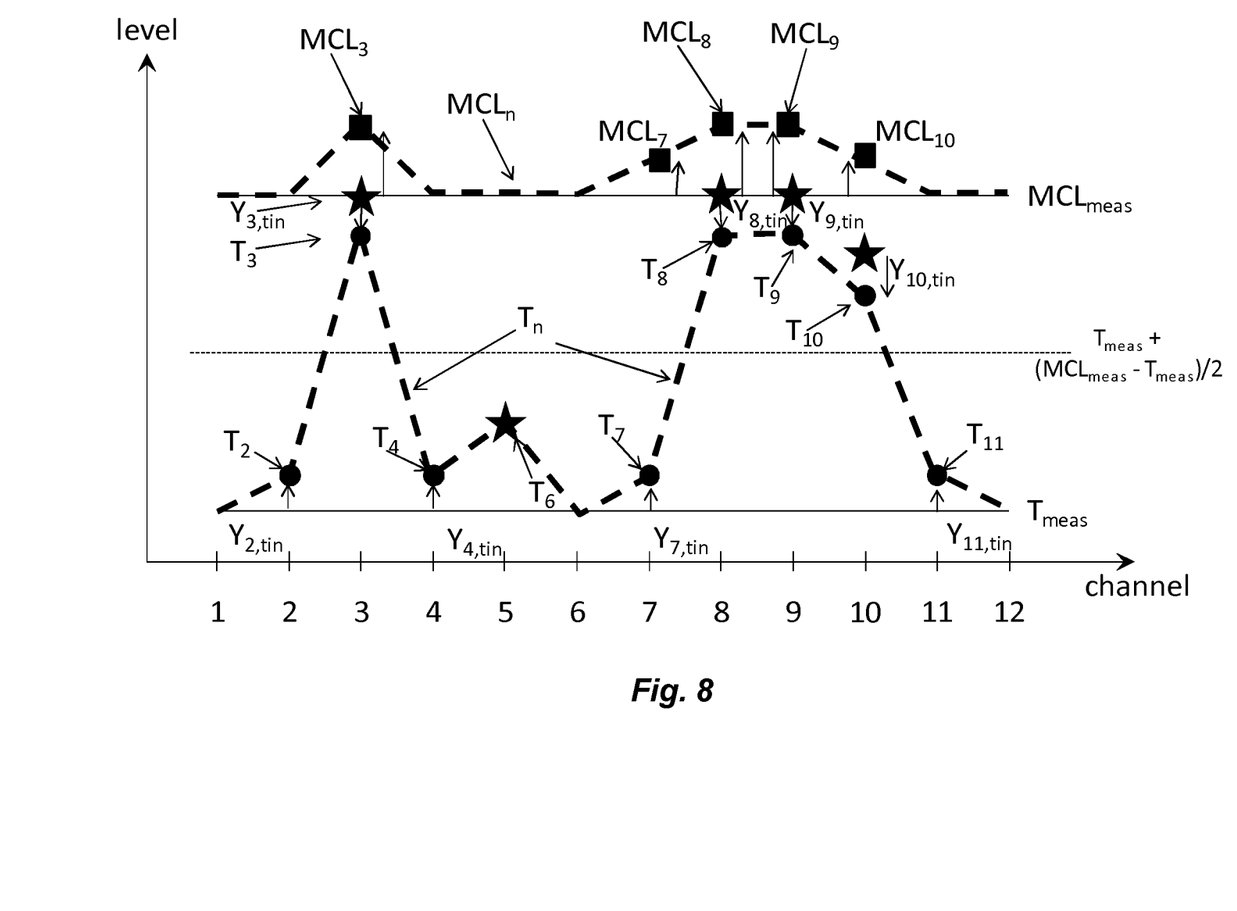
FIG. 8 shows a simplified graph of channel operating parameters with high tinnitus measured on many electrode contact channels.

Finally, FIG. 8 shows a simplified graph of channel operating parameters with very high tinnitus ($Y_{n,tin}>MCL_n$) perceived on electrode contact channels 3, 8 and 9. On electrode contact channels 1, 5 and 12, there is no perceived tinnitus and the adjacent channels n+1 and n−1 have no or low perceived tinnitus, so the adjusted channel threshold stimulation level $T_n$ is set to $T_{n,meas}$ where $w_n=1$. On electrode contact channels there is no perceived tinnitus and the adjacent channels n+1 and n−1 have high perceived tinnitus, then the adjusted channel threshold stimulation level $T_n$ is set to $T_{n,meas}$ where $w_n>1$ as on $T_2$, $T_4$, $T_7$ and $T_{11}$, and the adjusted channel maximum stimulation level $MCL_n$ is set to $MCL_{n,meas}$ where $v_n=1$ or $>1$ if linearly approximated, as on $MCL_7$ and $MCL_{10}$. For electrode contact channel 6, there is mild perceived tinnitus ($Y_{n,tin}<Z_n$), and the adjusted channel threshold stimulation level $T_n$ is set to the tinnitus weighted channel threshold stimulation level $T_n^*=w_n^* \ Y_n$ where $w_n^*=1$, while the adjusted channel maximum stimulation level $MCL_n$ is set to $MCL_{n,meas}$ where $v_n=1$. For electrode contact channel 10, there is high perceived tinnitus ($Y_{n,tin}>Z_n$), and the adjusted channel threshold stimulation level $T_n$ is set to the tinnitus weighted channel threshold stimulation level $T_n^*=w_n^* \ Y_n$ where $w_n^*<1$, while the adjusted channel maximum stimulation level $MCL_n$ is set to $MCL_{n,meas}$ where $v_n=1$. And for electrode contact channels 3, 8 and 9 where there is very high perceived tinnitus ($Y_{n,tin}>MCL_n$), the adjusted channel threshold stimulation level $T_n$ is set to the tinnitus weighted channel threshold stimulation level $T_n^*=w_n^* \ Y_n$ where $w_n^*<1$, while the adjusted channel maximum stimulation level $MCL_n$ is set to $MCL_{n,meas}$ where $v_n>1$.

In some embodiments, it may be useful to create several tinnitus fitting maps, which would differ according to how much tinnitus is masked. A first map could be created so that the tinnitus is completely (or maximally) masked. Then other maps would be set with gradually lowered values of adjusted channel threshold stimulation level $T_n$ of the affected electrode contact channels. Thus, the tinnitus fitting maps would be perceived from loudest to the softest. These might be applied for every electrode contact channel, or only for the channels most affected by tinnitus. Use of such tinnitus fitting maps may be especially helpful in patients afflicted with severe tinnitus (i e tinnitus occurring at very high levels or tinnitus affecting majority of the electrode contact channels) and very low dynamic range of the affected electrode contact channels. For example, if a patient has a very loud tinnitus and wants to be treated accordingly for his hearing impairment, the dynamic range on the affected electrode contact channels is relatively low. To offset that, the adjusted channel threshold stimulation level $T_n$ could be lowered somewhat to expand the dynamic range of the affected electrode contact channel. In some embodiments for patients with severe tinnitus, the adjusted channel maximum stimulation level $MCL_n$, also may be decreased on an affected electrode contact channel, which also would decrease the overall perceived volume.

If the tinnitus varies over time and/or pitch, the values of the channel tinnitus masking stimulation level $Y_{n,tin}$ also may vary. In such cases, the channel tinnitus masking stimulation level $Y_{n,tin}$ can be measured for each possible stage of tinnitus, and the highest value channel tinnitus masking stimulation level $Y_{n,tin}$ then used for calculations and fittings as described above.

The tinnitus contour and psychophysical thresholds also may change over time, and thus is it may be necessary to reperform the tinnitus fitting procedures from time to time. Usually, patients will need more frequent adjustment at the beginning of electrical stimulation treatment.

In contrast to using an ABI treatment only for compensation of hearing loss, compensation of tinnitus may be best achieved if only those electrode contacts are stimulated which are closest to the affected projections of the cochlear nucleus. Further, unlike use ABI stimulation for treatment of hearing loss, it may be necessary for tinnitus treatment that the electrode array covers all auditory projections. For that reason, the electrode paddle used may need to be larger.

Embodiments of the invention may be implemented in part in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments can be implemented in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A method of adjusting hearing implant operating parameters for a plurality of electrode contacts in an implantable electrode array to minimize tinnitus in an implanted patient, the method comprising:

measuring a channel tinnitus masking stimulation level for each electrode contact at which maximum tinnitus masking occurs, $Y_{tin,n}$;

measuring a channel threshold stimulation level for each electrode contact representing a lowest detectable stimulation level, $T_{meas,n}$;

measuring a channel maximum stimulation level for each electrode contact representing a maximum comfortable stimulation level, $MCL_{meas,n}$; and adjusting channel threshold stimulation level $T_n$ and channel maximum stimulation level $MCL_n$ for each electrode contact as a function of the channel tinnitus masking stimulation level $Y_{tin,n}$ and tinnitus masking stimulation levels for adjacent electrode contacts, $Y_{tin,adj}$.

2. The method according to claim 1, wherein the function adjusts the channel threshold stimulation level and channel maximum stimulation level for a given electrode contact based on a channel mean stimulation level $Z_n$ defined as a sum of the measured channel threshold stimulation level $T_{meas,n}$ and half the difference between the measured maximum stimulation level, $MCL_{meas,n}$ and the measured channel threshold stimulation level $T_{meas,n}$, wherein channel tinnitus is defined as low when the channel tinnitus masking stimulation level $Y_{tin,n}$ is less than channel mean stimulation level $Z_n$, and wherein channel tinnitus is defined as high when the channel tinnitus masking stimulation level $Y_{tin,n}$ is greater than channel mean stimulation level $Z_n$.

3. The method according to claim 2, wherein the function adjusts the channel threshold stimulation level $T_n$ and channel maximum stimulation level $MCL_n$ to the measured channel threshold stimulation level $T_{meas,n}$ and channel maximum stimulation level $MCL_{meas,n}$ for an electrode contact when channel tinnitus for the electrode contact and the adjacent electrode contacts is low.

4. The method according to claim 2, wherein the function adjusts the channel threshold stimulation level $T_n$ to be greater than the measured channel threshold stimulation level $T_{meas,n}$ for an electrode contact when channel tinnitus for the electrode contact is low, and channel tinnitus for at least one of the adjacent electrode contacts is high.

5. The method according to claim 2, wherein the function adjusts the channel threshold stimulation level $T_n$ to be less than the measured channel threshold stimulation level $T_{meas,n}$ for an electrode contact when channel tinnitus for the electrode contact is high.

6. The method according to claim 2, wherein the function adjusts the channel maximum stimulation level $MCL_n$ to be greater than the measured channel maximum stimulation level $MCL_{meas,n}$ for an electrode contact when the channel tinnitus masking stimulation level $Y_{tin,n}$ equals or exceeds the measured channel maximum stimulation level $MCL_{meas,n}$.

7. The method according to claim 1, wherein there is a dynamic range of at least 1 dB between the adjusted channel threshold stimulation level $T_n$ and the channel maximum stimulation level $MCL_n$.

8. The method according to claim 1, wherein the electrode array is a cochlear implant electrode array.

9. The method according to claim 1, wherein the electrode array is an auditory brainstem implant electrode array.

10. The method according to claim 1, wherein the plurality of electrode contacts are arranged in a one-dimensional array on the electrode array.

11. The method according to claim 1, wherein the plurality of electrode contacts are arranged in a two-dimensional array on the electrode array.

\* \* \* \* \*